United States Patent [19]

Charneski et al.

[11] Patent Number: 4,675,301
[45] Date of Patent: Jun. 23, 1987

[54] METHOD FOR CORRECTING FOR CHANGES IN AIR PRESSURE ABOVE A LIQUID TO BE DISPENSED FROM A CONTAINER MOUNTED ON A PROBE

[75] Inventors: David M. Charneski, Rochester; James D. Shaw, Hilton, both of N.Y.

[73] Assignee: Eastman Kodak Company, Rochester, N.Y.

[21] Appl. No.: 718,319

[22] Filed: Apr. 1, 1985

[51] Int. Cl.$^4$ .................... B65D 83/14; B67D 5/08; G01N 1/10; G01N 1/14
[52] U.S. Cl. .................... 436/180; 73/863.01; 73/864.35; 222/61; 222/396; 222/397; 422/100
[58] Field of Search .................... 422/100; 73/863.01, 73/863.02, 863.83, 863.84, 864.15, 864.18, 864.35; 222/61, 396, 397, 420; 436/180, 179

[56] References Cited

U.S. PATENT DOCUMENTS 3,992,158 11/1976 Przybylowicz et al. .
4,041,995 8/1977 Columbus .
4,053,381 10/1977 Hamblen et al. .
4,258,001 3/1981 Pierce et al. .
4,287,155 9/1981 Tersteeg et al. .
4,340,390 7/1982 Collins et al. .
4,452,899 6/1984 Alston .

Primary Examiner—David L. Lacey
Assistant Examiner—C. M. Delahunty
Attorney, Agent, or Firm—Dana M. Schmidt

[57] ABSTRACT

There is disclosed dispensing apparatus using a container for liquid, the apparatus comprising pressurizing means for aspirating liquid into the container, and for pressurizing liquid within the container to dispense the liquid. To control the ambient pressure of the atmosphere above the liquid within the container, system control means and a method of control are provided. Such means and the corresponding step of the method comprise (a) means for repeatedly sensing the air pressure above the level of the liquid within such container, and for repeatedly generating a signal corresponding to said pressure;
(b) means for reading and storing the signal when it represents a desired baseline air pressure;
(c) means for storing a tolerance factor;
(d) means for determining the difference between the signal stored by means (b) and the signal repeatedly generated by the sensing means, as a difference value; and
(e) actuating means for activating the pressurizing means to produce a negative or positive pressure differential when the determining means (d) detects that the absolute value of the difference value is greater than the value of the stored tolerance factor.

2 Claims, 12 Drawing Figures

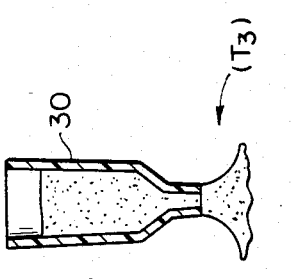
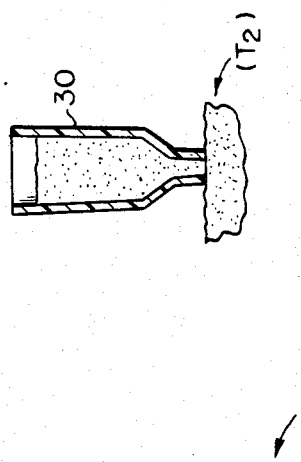
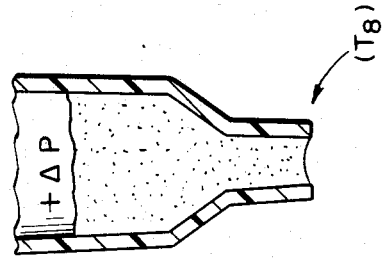
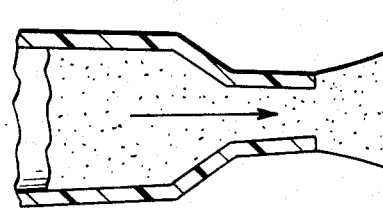
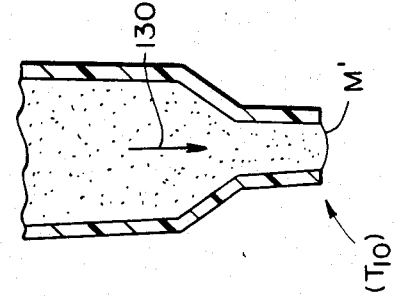
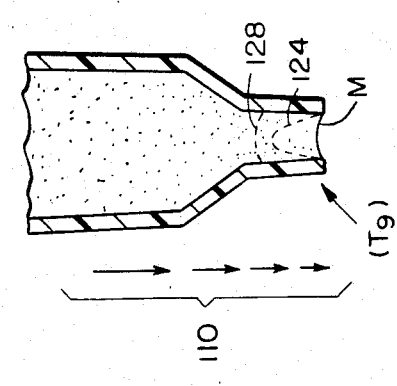

METHOD FOR CORRECTING FOR CHANGES IN AIR PRESSURE ABOVE A LIQUID TO BE DISPENSED FROM A CONTAINER MOUNTED ON A PROBE

FIELD OF THE INVENTION

This invention relates to apparatus for aspirating liquid into a container, and for dispensing such aspirated liquid. More specifically, it relates to apparatus and a method for controlling the pressure within such container to achieve greater uniformity in dispensing.

BACKGROUND OF THE INVENTION

Liquid dispensers have been used in analyzers for the detection of the concentration of liquid analytes using as analysis means, test elements that contain within themselves the necessary reagents to permit such detection. Examples of such analyzers are described in U.S. Pat. Nos. 4,287,155, issued Sept. 1, 1981, and 4,340,390, issued July 20, 1982. Examples of such test elements appear in U.S. Pat. Nos. 3,992,158, issued Nov. 16, 1976; 4,053,381, issued Oct. 11, 1977; and 4,258,001, issued Mar. 24, 1981. The conventional method for dispensing liquid onto such test elements using such analyzers has been to aspirate test liquid from a relatively large container, into a dispensing container. The dispensing container is then moved to a position immediately above such a test element, and a fraction (e.g., 10 µl) of the aspirated liquid is dispensed. The dispensing container is fluidly connected, in such analyzers, to a pressurizing means. Such means generates both the operative partial vacuum needed to aspirate an amount of liquid into the container, and the partial pressure operative to dispense that aspirated liquid, in fractional amounts, onto a plurality of test elements. A pressure transducer is also conventionally included to ascertain the pressure within the container, so as to detect the occurrence of the desired dispensing event versus a failure to dispense. A microprocessor generally is used to control the apparatus in response to the conditions sensed.

Because only a fraction of the liquid is dispensed each time, one prior approach to dispensing liquid onto a test element has been to vent the dispensing container after each dispensing event. Such an approach is described in U.S. Pat. No. 4,041,995, issued by R. L. Columbus on Aug. 16, 1977, and in U.S. Pat. No. 4,452,899 (col. 4, lines 34–40 issued by Wilton Alston on June 5, 1984. Although this approach generally has worked satisfactorily, on occasion the volume of liquid so dispensed has deviated from that desired. This occurs as follows:

As is described in the aforesaid '899 patent, movement of the dispensing probe into position directly above a test element can cause prespotting of the test element when the probe decelerates to a stop, unless the process includes a partial withdrawal of the meniscus in the dispensing aperture. Such partial withdrawal is achieved by backing up the dispensing pump of the pressurizing means enough to create a slight partial vacuum. This in turn requires any vent that is present to be closed, and remain closed during the actual dispensing step. While the vent is closed, evaporation of the liquid can occur, causing a ΔP pressure to build in the air above the liquid in the dispensing container. Such build-up of pressure adds to the pressure delivered during dispensing, so as to cause a larger volume to be dispensed than would be the case if no build-up had occurred, e.g., if venting had occurred immediately before dispensing. The build-up of pressure can also occur when venting cannot be used. An example of this is those instances when a relatively large volume of liquid (e.g., 110–230 µl) is present in the dispensing container. In that case, the vent is kept closed between dispensing events, because the weight of the large volume would cause the liquid to run out of the container if the vent were open. In other words, at large liquid volumes it has been the practice to operate such dispensing apparatus as though no vent were present. Because the vent is closed, a build-up of pressure tends to occur.

Regardless of the reason for the build-up in air pressure, it is relatively unpredictable. Thus it cannot be compensated for on an a priori basis. As a result, significant deviations from the desired volume can occur in an unpredictable fashion, for example, as much as 10%.

The problem then, prior to this invention, has been to provide such a dispensing apparatus that achieves greater uniformity in the amount of liquid that is dispensed.

SUMMARY OF THE INVENTION

This invention is based on the discovery that the pressurizing means can be used to control the internal air pressure within the dispensing container, thus preventing pressure changes that lead to altered dispensed volumes.

More specifically, in accord with one aspect of the invention there is provided a dispensing control system in apparatus for dispensing liquid which includes a probe for mounting a container having a dispensing aperture and pressurizing means fluidly connected to the probe for generating an operative positive or negative pressure differential relative to atmospheric pressure, within a mounted container, whereby liquid is expelled from or drawn into, respectively the container via the dispensing aperture. The control system comprises (a) means for repeatedly sensing the air pressure above the level of the liquid within such container, and for repeatedly generating a signal corresponding to the pressure;

(b) means for reading and storing the signal when it represents a desired baseline air pressure;

(c) means for storing a tolerance factor;

(d) means for determining the difference between the stored signal and the signal repeatedly generated by the sensing means, as a difference value; and (e) actuating means for activating the pressurizing means to produce a negative or positive pressure differential when the determining means (d) detects that the absolute value of the difference value is greater than the value of the stored tolerance factor.

As a result, any positive or negative pressure change within such container is compensated by the negative or positive pressure differential produced when the repeatedly sensed signal exceeds acceptable limits, for example ±3 mm of water.

In accord with another aspect of the invention, there is provided a dispensing method using such apparatus, comprising the steps noted for means (a) through (e) recited in the previous paragraph.

Thus, it is an advantageous effect of the invention that the amount of liquid dispensed by the apparatus is more accurately controlled within the desired limits.

It is a further advantageous effect of the invention that the need for a venting means has been eliminated.

Other advantageous effects will be readily apparent from the following Description of the Preferred Embodiments when read in light of the attached drawings.

BRIEF DESCRIPTION OF THE DRAWINGS

FIGS. 4A through 4C are fragmentary sectional views illustrating the stages of aspiration through which the dispensing container is processed relative to the supply of patient sample;

FIGS. 5A through 5D are fragmentary sectional views similar to FIGS. 4A-4C, except illustrating the stages through which the dispensing container is processed after aspiration, including dispensing;

DESCRIPTION OF THE PREFERRED EMBODIMENTS

The invention is particularly useful in colorimetric and potentiometric assays using analyzers and dried test elements of the type described in the above-noted patents. In addition, the invention is useful in any dispensing apparatus or method which aspirates liquid after moving the dispensing container from the atmosphere into a liquid phase, regardless of the steps that follow the dispensing of the aspirated liquid, and regardless of whether the dispensing is onto a test element.

Terms such as "up", "down", "lower", "vertical", "horizontal", and "bottom", as used herein refer to the orientation of parts when the apparatus is positioned in its customary position of use.

Figure 1:
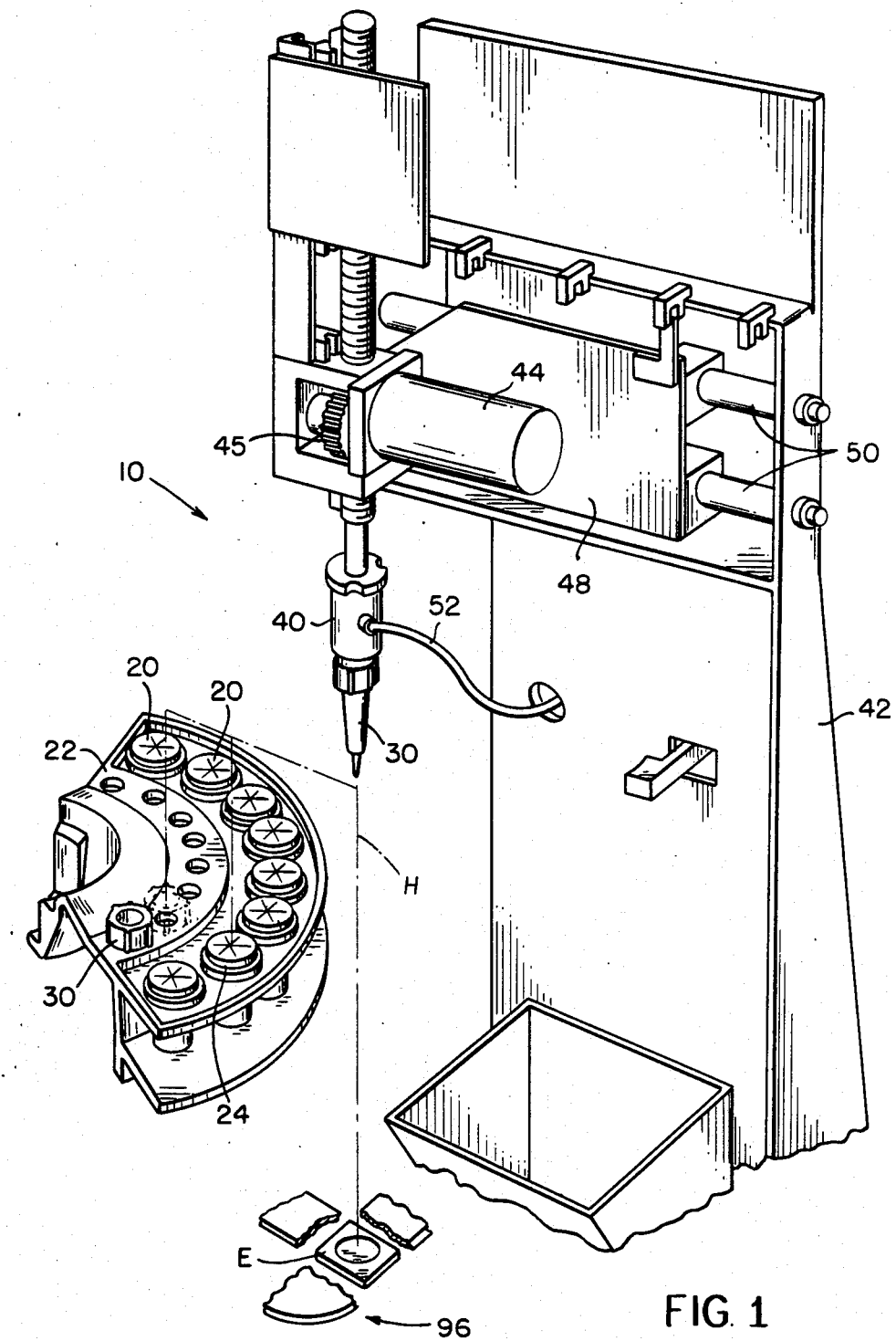
FIG. 1 is a fragmentary perspective view of a dispensing apparatus with which the invention can be practiced.
Figure 2:
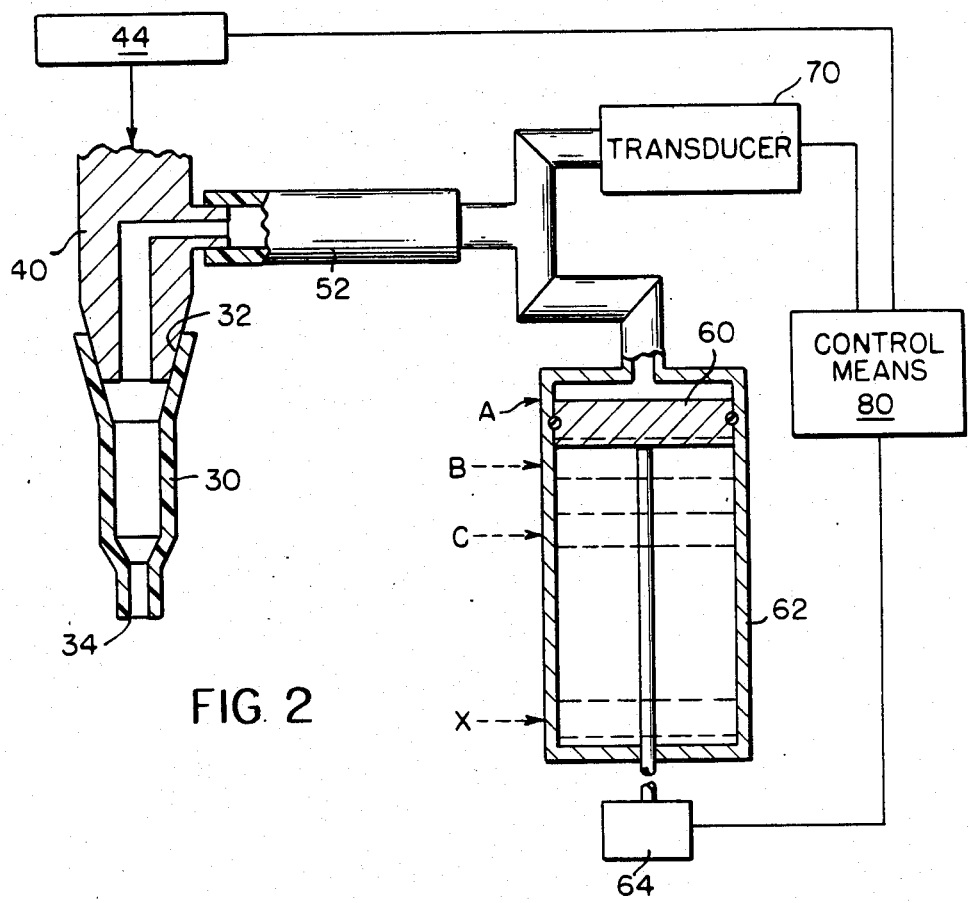
FIG. 2 is a fragmentary, partially schematic view illustrating certain details of the dispensing apparatus, wherein parts and positions are not shown to scale.

A portion of a preferred dispensing apparatus 10 is illustrated in FIGS. 1 and 2. A plurality of relatively large sample containers 20 is provided in a tray 22, which also supports removable, preferably disposable dispensing containers 30. The purpose of the apparatus is to transfer liquid from container 20 to container 30, and then dispense from container 30. The containers 30 have, FIG. 2, a larger aperture 32 at one end to mate with a probe 40, and a smaller aperture 34 at the opposite end for aspirating and dispensing. Each of containers 20 is preferably provided with a pierceable closure or cap 24, FIG. 1. The probe 40 mounts the containers 30. Preferably probe 40 is mounted for vertical and horizontal movement on a frame 42, such movement being provided respectively by a motor 44 and gear 45, and by a car 48 carrying the probe 40 horizontally on rails 50. Motor 44 can be a stepper motor or a D.C. motor with feedback control. The combined movement of the car and probe is effective to carry the probe within the plane noted as "H", FIG. 1. Test elements E are held by members 96 so as to intersect plane H, to permit dispensing of the liquid from container 30 onto the test element.

The movement of probe 40 relative to containers 20 and test elements E is, of course, optional and of no direct consequence, except as hereinafter noted, to the control of pressures within containers 30 provided by this invention. Thus, an equally useful alternative arrangement would be one in which probe 40 is stationary, and containers 20 and elements E are moved into place relative to probe 40.

A pressure line 52 provides a partial vacuum or a partial pressure, relative to atmospheric, to a dispensing container 30 picked up by the probe. The pressure or vacuum is provided by means such as a piston 60 and piston chamber 62, FIG. 2, driven by appropriate motor means 64. For example, movement of piston 60 from position "A" through positions B and C down to position "X" creates the operative partial vacuum that aspirates the liquid from container 20 into container 30 at the appropriate time. A pressure transducer 70 is used to sense the pressure in container 30, for example to determine when proper dispensing of the liquid out of container 30 occurs.

Alternatively, piston chamber 62 and its piston can be part of probe 40 so as to move up and down with the probe.

Figure 3:
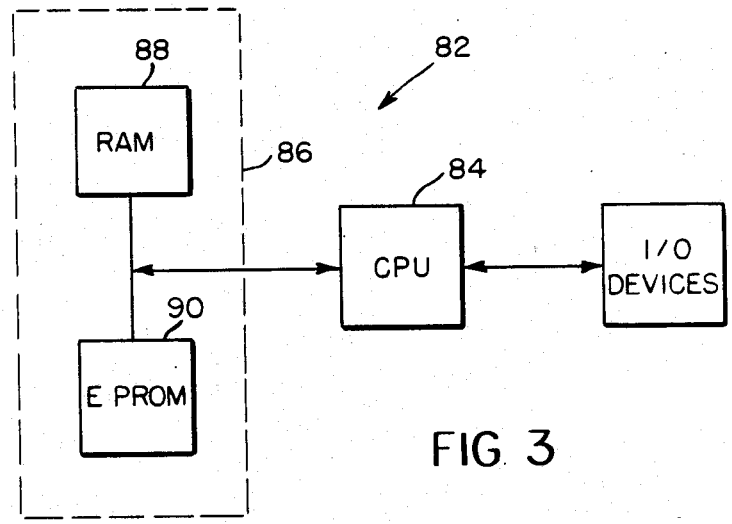
FIG. 3 is a schematic illustration of a microprocessor useful as a control means.

Appropriate control means 80 are provided to coordinate the actuation of motor 44 and motor 64, in response to conditions sensed by e.g., transducer 70. Control means 80 can comprise a microprocessor or hard-wired logic circuits. Most preferably, it includes a microprocessor 82, FIG. 3, particularly in light of the programming discussed hereinafter. As is conventional, such a microprocessor comprises a central processing unit 84, for example, an Intel 8085 chip, and memory unit 86 comprising one or more RAM's 88 and optionally one or more E PROM's 90. The microprocessor preferably is also wired to standard input/output devices, as shown, if the dispensing apparatus is part of a complete analyzer.

The aforedescribed comprise a conventional dispensing apparatus. Such apparatus is also controlled conventionally via microprocessor 82 to provide the following conventional aspirating and dispensing events (FIGS. 4–6): To aspirate liquid into container 30, FIGS. 4A–4C, such container is first moved downwardly into the liquid supplied by a container 20, FIG. 4A. When negative pressure is supplied via probe 40 to container 30 at a time $T_1$, such differential pressure will cause the liquid to rise into container 30, FIG. 4B, which is completed by time $T_2$. Thereafter, container 30 is withdrawn from the supply of liquid, arrow 100, FIG. 4C, and moved towards the station at which liquid is to be dispensed, FIG. 5A, preferably onto test element E. When the probe begins to decelerate, as suggested by arrows 10 of decreasing length, a negative pressure is preferably drawn onto the liquid to pull meniscus M, shown first as a solid line, back to dotted line 124 but preferably not to dotted line 128. As explained in the aforesaid U.S. Pat. No. 4,452,899, this serves to prevent the deceleration from prematurely ejecting small amounts of liquid onto a test element. Thereafter, FIG. 5B, a slight increase in pressure is provided, arrow 130, to cause a convex meniscus M'. This is followed, FIG. 5C, by the actual dispensing of the liquid caused by a large increase in pump pressure.

Because this much of the control of aspiration and dispensing is conventional, further explanation of the logic used to program microprocessor 82 to achieve this is unnecessary.

Figure 6:
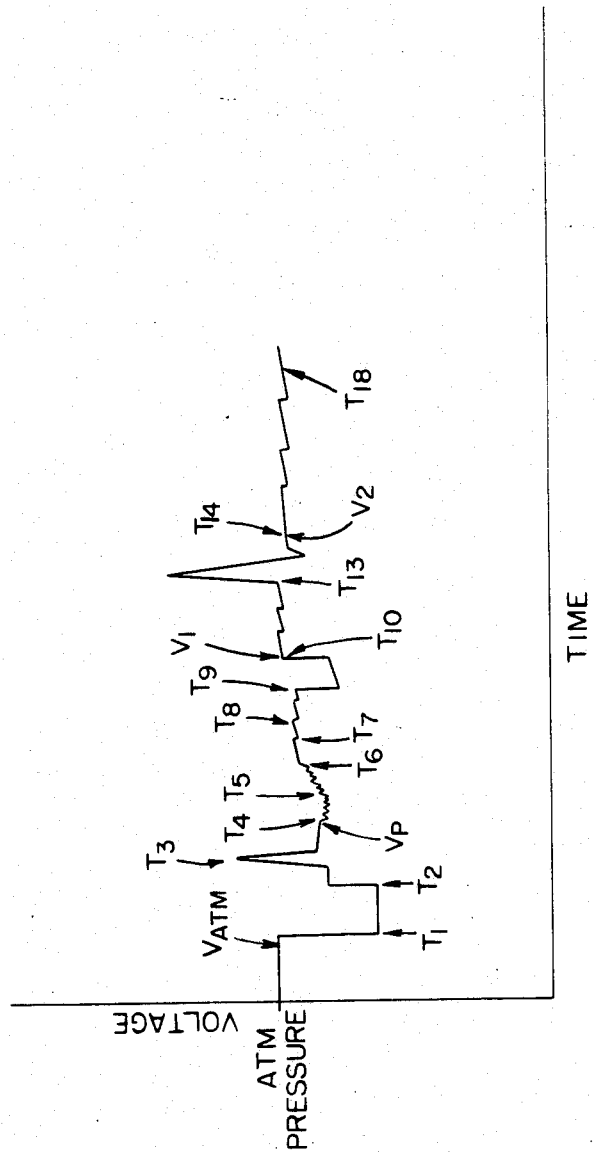
FIG. 6 is an example of a voltage versus time signal trace generated by a transducer when carrying out the steps of the invention, the time units being arbitrary.

The pressure changes discussed above that occur in the air volume in container 30 above the liquid are shown in the pressure trace of FIG. 6, wherein pressures are represented by the voltage output of transducer 70 against time. At time $T_1$, piston 60 is withdrawn towards position X, FIG. 2, to initiate conditions that will lead to aspiration. This corresponds to the container condition shown in FIG. 4A. As flow begins into container 30, time $T_2$ the trace reverses its negative direction until aspiration is completed, FIG. 4B. Preferably, to eject a small fraction of aspirated liquid back into container 20 and thus to force the upper meniscus into a concave shape, a small positive pressure is applied by piston 60, creating a positive preliminary spike shown at $T_3$, FIG. 6. Otherwise, additional stored energy in a convex meniscus adds unacceptably to dispensed quantity volume. Thereafter, container 20 is withdrawn from the external liquid, FIG. 4C, at a time $T_4$, creating a dithering variation in the trace of FIG. 6. At time $T_9$, motor 64 is activated to withdraw piston 60, to create a sharply concave meniscus as shown as line 124, FIG. 5A, preparatory to deceleration by probe 40 as it approaches the test element. At time $T_{10}$, after the container has completed its motion, motor 64 is reversed to create a slight increase in pressure, pushing the concave meniscus out to a convex position M', FIG. 5B. Thereafter, a large spike of positive pressure is delivered by motor 64 and piston 60, time $T_{13}$, FIGS. 5C and 6, to force the desired quantity of liquid to dispense.

In accord with one aspect of the invention the apparatus described above is used to provide a more accurate volume of dispensed liquid as follows: Piston 60 is controlled in response to transducer 70 and through the use of microprocessor 82, to override any build-up or lessening of pressure such as would otherwise unacceptably alter the dispensed volume. It has been found that this is done most preferably in conjunction with the elimination of the vent means conventionally interposed in pressure line 52 (FIG. 2.) The elimination of the vent means has the advantage that such vent means is usually the first component in the described pressure system to develop leaks.

At various stages there is a time, FIG. 5D, before the next dispensing event when pressure $\Delta P$ can be built up, as by evaporation. This pressure change is compensated for, first, by detecting a change in excess of an acceptable threshold defined herein as tolerance factor, and second by incrementally advancing or withdrawing piston 60 a predetermined distance by incrementally advancing or withdrawing motor 64 a predetermined number of half-steps, for example, one.

Referring again to the pressure curve represented by the voltage output in FIG. 6, of the transducer, a baseline pressure is read at various appropriate times. The purpose for reading this pressure is to establish a baseline against which subsequent pressures are subtracted, and the difference compared to a tolerance factor, stored as a value $V_{Tol}$. $V_{Tol}$ is selected to be large enough to accommodate trivial and temporary variations, but small enough to allow detection of harmful variations that exceed acceptable limits. $V_{Tol}$ is either preset at the factory, or provided as a calibration value.

The baseline pressure is reread and restored as an updated value on different occasions, because the desired baseline pressure changes as the conditions change. The first of these times is at $T_4$, after the ejection of some of the aspirated liquid has occurred at time $T_3$. The baseline pressure is read as a post prime voltage, labeled $V_P$. At this point, an offset pressure value, $V_{off}$, discussed in detail hereafter, is added and the sum stored in memory, since no dispensing has occurred yet from this particular container. In addition, the microprocessor memory includes the stored tolerance factor, as a $\pm V_{Tol}$, for example, $\pm 40$ mv. Thus, after container 30 has been withdrawn from the source of liquid (time $T_4$ to $T_5$) the sum of $(V_P+V_{off})$ is stored for later use, that is, when the pressure monitoring algorithm hereinafter described, is enabled. The microprocessor enables the transducer 70 to monitor the pressure conditions in dispensing container 30 above the liquid commencing with time $T_5$, FIG. 6. The first result is to force the pump motor to raise the pressure to a value of $V_P+V_{off}$ by time $T_6$. Preferably, the monitoring algorithm is then disabled while the probe accelerates to a constant velocity, time $T_7$. As evaporation takes place, time $T_7$ to time $T_9$, FIGS. 5D and 6, a $\Delta P$ increase in pressure takes place. This continues until the transducer detects that the increased pressure exceeds $V_i$ plus the tolerance factor $V_{Tol}$. (At times $T_7$ to $T_9$, $V_i=V_P+V_{off}$.) At such a time $T_7$ and $T_8$, FIG. 6, motor 64 is activated to, in this case, withdraw piston 60 a predetermined amount, for example, an amount corresponding to onehalf a step of the motor (such as position B or C in FIG. 2). As a result, the internal air pressure is returned to the baseline value $V_i$.

As noted above, at various times in the cycle of operation, probe 40 accelerates, and under the preferred method of operation, the pressure monitoring algorithm is disabled at such times. This result in a disabling of the steps of determining the difference between the stored signal ($V_i$) and the signal representing the sensed pressure; as well as the step of altering the air pressure by activating motor 64. Another such algorithm-disabling time is time $T_9$, which allows a negative pressure to be drawn on the liquid by pump 64. As described for FIG. 5A, this allows the probe and container 30 to decelerate without causing premature ejection of liquid.

Thereafter, the pressure monitor algorithm is re-enabled at time $T_{10}$, and a new baseline pressure $V_1$ is read and stored. Such new reading is necessitated by the fact that the expected baseline pressure plus $V_{off}$ may be higher than $V_P+V_{off}$ at time $T_6$, due to a slight rising of the liquid meniscus in aperture 34 of the container. If the old sum $V_P+V_{off}$ were to continue to be used, excessive dispensed volume would occur at time $T_{13}$, if not premature dispensing.

Starting with time $T_{10}$, and in the manner described above, transducer 70 initiates a half-step retreat of the motor at various times between $T_{10}$ and $T_{13}$ when the test pressure detected exceeds the allowed value of $V_1$ plus $V_{Tol}$.

At time $T_{13}$, dispensing commences as noted above for FIG. 5C. During this part of the cycle, the pressure monitoring algorithm is disabled, and then re-enabled at time $T_{14}$. At this time, yet another baseline pressure is read and stored, namely $V_2$. The reason is that the value the internal air pressure should be, decreases after each quantity is dispensed. The amount of decrease equals, of course, the decrease in static head of pressure due to the remaining height of liquid to be dispensed. Thereafter, the pressure is monitored and corrected during time $T_{14}$ to $T_{18}$, as before, until the next dipensing event or until the probe accelerates.

As a result of the corrective steps taken at, e.g., time $T_8$ and between times $T_{10}$ and $T_{13}$ or $T_{14}$ and $T_{18}$, a more constant pressure is maintained in the atmosphere above the liquid of container 30, and a more uniform volume is dispensed during each subsequent dispense cycle.

It will also be appreciated that a negative pressure change can occur that will be monitored by the pressure transducer as a ΔV in excess of $-V_{Tol}$, that necessitates an increase in pressure provided by a one-half step advance by motor 64. For example, in some cases cooling can cause a pressure decrease.

Figure 7:
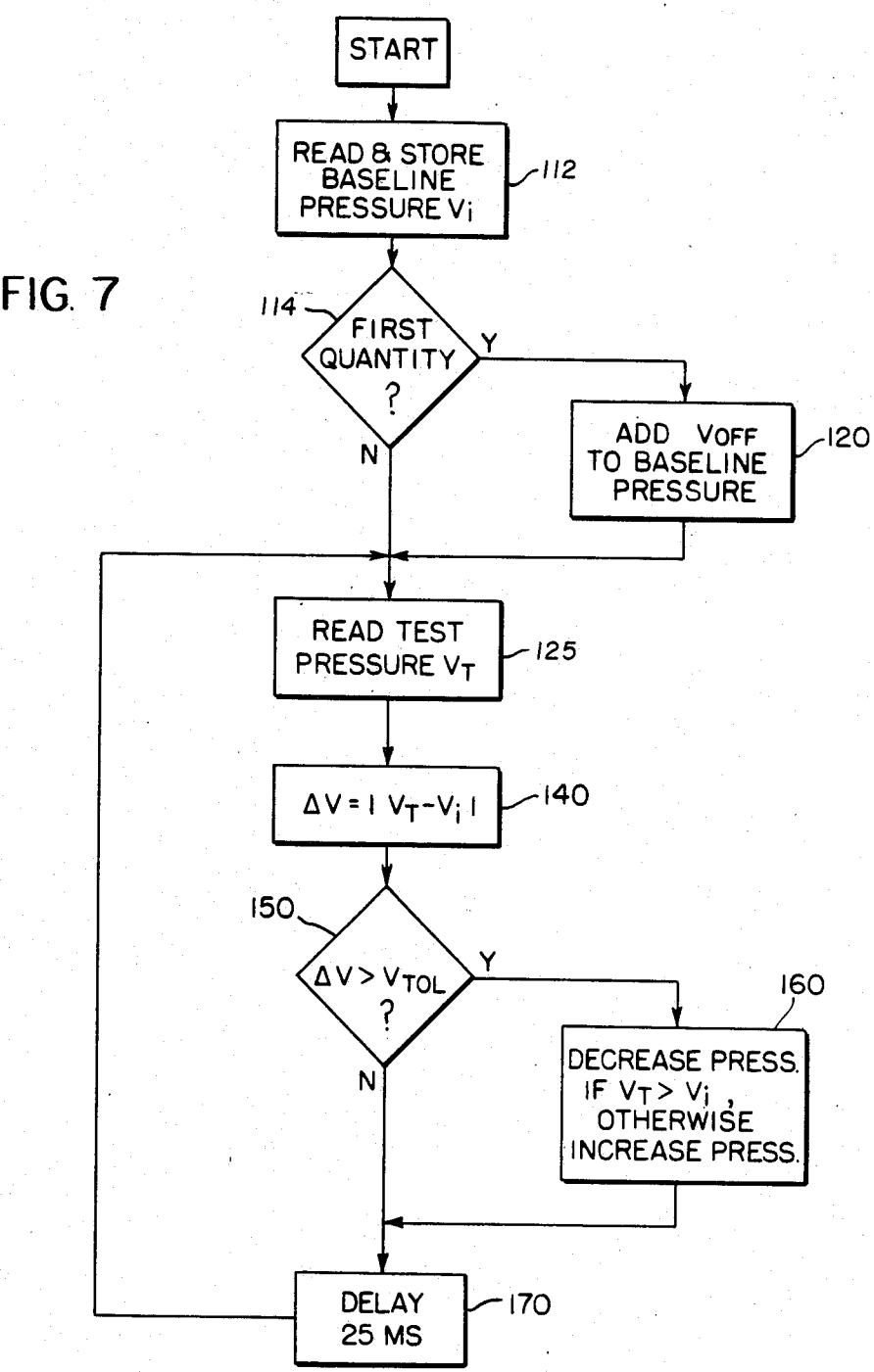
FIG. 7 is a flow chart for programming the control means of the described apparatus to carry out the invention.

A flow chart useful in programming microprocessor 82 for the monitoring algorithm, using conventional programming techniques, appears in FIG. 7. The monitoring algorithm is a subroutine that is activated by the rest of the program of the microprocessor to function only while probe 40 is undergoing no acceleration or deceleration. Such a condition occurs at predetermined points in the sequencing of the analyzer, so that interrupts at predetermined points in the sequencing can be used to enable and disable this subroutine. As will be readily apparent, the algorithm routine is disabled, FIG. 6, e.g., during times $T_6$–$T_7$, and times $T_9$ and $T_{10}$.

The first algorithm step 112, FIG. 7, is to read and store in memory of the microprocessor a baseline pressure, which is generated as a voltage $V_i$ produced by pressure transducer 70 for i=P, 1, 2, etc. Thus, the first such baseline pressure for a given container 30 is $V_P$ as noted above, then $V_1$, $V_2$, etc. Next, the microprocessor interrogates, step 114, as to whether the next drop to be dispensed is the first drop to be dispensed from a given container 30. If and only if a microprocessor flag indicates that it is, then step 120 is carried out to add a suitable offset value, $V_{off}$ such as 100 mv, to the baseline pressure reading $V_P$. Because of the nature of the problem being corrected, $V_{off}$ is larger than $V_{Tol}$. As noted, this causes motor 64 to advance to increase the pressure within probe 40. This increase in pressure just for the first drop metering has been found to give better metering results for that first drop.

Thereafter, the algorithm continues by reading the test pressure, step 125, as evidenced by the voltage $V_T$ of transducer 70. This value is then used to create a pressure difference ΔV, which is calculated, step 140, as the absolute value of $V_T - V_i$. Next, step 150, the microprocessor queries as to whether ΔV so defined is greater than the tolerance factor $V_{Tol}$ permanently left in memory. ($V_{Tol}$ may be stored in the same, or different, memory means as $V_i$.) If yes, the microprocessor further calculates, step 160, whether $V_T > V_i$ or not. If the former, the microprocessor sends out a signal to motor 64 to withdraw piston 60 a small amount, such as by one-half a step, to decrease the pressure in container 30. If the latter condition is determined ($V_i > V_T$), then microprocessor 82 sends a signal to motor 64 to advance that small amount, e.g., ½ a step, to increase pressure within container 30.

In the meantime, step 170 is executed which runs a delay clock for a suitable time, such as 25 milliseconds, before looping back to step 130 to repeat the sequence. The 25 millisec delay is used to allow transient oscillations in pressure to die out before making another test reading.

It will be appreciated that an alternative procedure to that just described, which is the mathematical equivalent, is to (a) determine whether $V_T$, the signal for the test pressure, is larger or smaller than $V_i$, (b) if $V_T$ is larger, then determine whether $V_T$ exceeds the value of $V_i + V_{Tol}$, otherwise determine whether $V_T$ is less than $V_i - V_{Tol}$, and (c) if step (b) determines that $V_T$ exceeds ($V_i + V_{Tol}$) or is less than ($V_i - V_{Tol}$), then initiating a small pressure decrease or increase, respectively, by activating the pump motor a small amount and in the proper direction.

The invention has been described in detail with particular reference to preferred embodiments thereof, but it will be understood that variations and modifications can be effected within the spirit and scope of the invention.

What is claimed is:

1. A method for correcting for changes in air pressure above a liquid to be dispensed from a container mounted on a probe, using pressurizing means fluidly connected to said probe for generating an operative positive or negative pressure differential relative to atmospheric pressure, within a mounted container; the method comprising the steps of
   (a) repeatedly sensing and repeatedly generating as a corresponding electrical signal, the air pressure above the level of the liquid within such container;
   (b) reading and storing said signal at at least one time when it represents a desired baseline air pressure;
   (c) determining the difference between said stored signal and the signal repeatedly sensed in step (a) as a difference value; and
   (d) altering said air pressure above said liquid in said container without venting said container to the atmosphere, said altering step comprising activating said pressurizing means to produce a negative or positive pressure differential when said determining step (c) detects that the absolute of said difference value is greater than the value of a stored tolerance factor,
   whereby any positive or negative pressure change within such container is compensated by said step (d) providing a negative or positive pressure change, respectively, when said repeatedly sensed signal generated by step (a) exceeds the limits of acceptable deviations.

2. A method as defined in claim 1, further including the step of disabling at least said steps (c) and (d) while said probe experiences a change in velocity.

* * * * *

UNITED STATES PATENT AND TRADEMARK OFFICE
CERTIFICATE OF CORRECTION

PATENT NO. : 4,675,301

DATED : June 23, 1987

INVENTOR(S) : David M. Charneski and James D. Shaw

It is certified that error appears in the above-identified patent and that said Letters Patent are hereby corrected as shown below:

Column 1, line 48, "lines 34-40 issued" should read --lines 34-40) issued--.

Column 6, line 24, "onehalf" should read --one-half--.

Column 8, line 44, "absolute of" should read --absolute value of--.

Signed and Sealed this

Thirty-first Day of May, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,675,301

DATED : June 23, 1987

INVENTOR(S) : David M. Charneski et al

It is certified that error appears in the above-identified patent and that said Letters Patent are hereby corrected as shown below:

Column 8, line 3, "step 130" should read --step 125--.

Signed and Sealed this

Twenty-third Day of August, 1988

Attest:

DONALD J. QUIGG

Attesting Officer

Commissioner of Patents and Trademarks